United States Patent [19]

Margolin

[11] Patent Number: 5,316,944
[45] Date of Patent: May 31, 1994

[54] ENZYMATIC RESOLUTION OF A RACEMIC MIXTURE OF GAMMA-AMINO ACIDS USING PENICILLIN ACYLASE

[75] Inventor: Alexey L. Margolin, Cincinnati, Ohio

[73] Assignee: Merrell Dow Pharmaceuticals, Cincinnati, Ohio

[21] Appl. No.: 915,446

[22] Filed: Jul. 17, 1992

[51] Int. Cl.$^5$ .............................................. C12P 41/00
[52] U.S. Cl. .................................................... 435/280
[58] Field of Search ........................................... 435/280

[56] References Cited

U.S. PATENT DOCUMENTS 4,454,156  6/1984  Casara ................................ 424/319
4,636,470  1/1987  Empie ................................ 435/280

OTHER PUBLICATIONS

D. Rossi, et al., The Use of Benzylpenicillinacylase From *Escherichia Coli* In The Resolution of Some Racemic β-, γ-, δ-, and ε-Amino-Acids, Experientia, 33(12), 1557-1559 (1977).

Claudio Fuganti, et al., Substrate Specificity and Enantioselectivity of Penicillinacylase Catalyzed Hydrolysis of Phenacetyl Esters of Synthetically Useful Carbinols, *Tetrahedron*, 44(9), 2575-2582 (1988).

D. Rossi, et al., Hydrolysis of N-Phenylacetyl-α-methyl-α-amino Acids By Benzylpenicillinacylase, *Experientia*, 41, 35-37 (1985).

H. Waldmann, A New Access to Chiral 2-Furylcarbionols By Enantioselective hydrolysis With Penicillin Acylase, *Tetrahedron Letters*, 30(23), 3057-3058 (1989).

M. Jung, et al., Mechanism of the Stereospecific Irreversible Inhibition of Bacterial Glutamic Acid Decarboxylase by (R)-(−)-4-Aminohex-5-ynoic Acid, An Analogue of 4-Aminobutyric Acid, *Biochemistry*, 17(13), 2628-2632 (1978).

Jones JB, Tetrahedron 42:3351-3403 (1986).
Rossi, D. J. Org. Chem. 43:2576-81 (1978).

*Primary Examiner*—Douglas W. Robinson
*Assistant Examiner*—S. Saucier
*Attorney, Agent, or Firm*—Michael J. Sayles

[57] ABSTRACT

The present invention relates to the enzymatic resolution of a racemic mixture of stereospecific, pharmaceutically useful in vivo inhibitors of γ-aminobutyric acid transaminase (GABA-T), specifically γ-ethynyl GABA, γ-vinyl GABA and γ-allenyl GABA using penicillin acylase (PA).

4 Claims, No Drawings

ENZYMATIC RESOLUTION OF A RACEMIC MIXTURE OF GAMMA-AMINO ACIDS USING PENICILLIN ACYLASE

FIELD OF THE INVENTION

This invention relates to the enzymatic resolution of a racemic mixture of stereospecific, pharmaceutically useful in vivo inhibitors of γ-aminobutyric acid transaminase (GABA-T).

BACKGROUND OF THE INVENTION

γ-Aminobutyric acid (GABA) is an important inhibitory neurotransmitter. When the concentration of GABA in the brain decreases below a threshold level, seizures and other neurological disorders occur (A. V. Delgado-Escueta et al., Basic Mechanisms of the Epilepsies, Raven Press, New York, 365 (1986)). The appropriate level of GABA at the synaptic cleft can be maintained by the irreversible inactivation of the enzyme GABA-T, which is involved in the degradation of GABA (S. M. Nanavati et al., J. Med Chem., 32, 2413 (1989)).

The biotransformation of γ-aminobutyric acid (GABA) to succinic acid semialdehyde, which is catalyzed by the enzyme GABA-transaminase (GABA-T), is the primary reaction responsible for the catabolism of GABA, an inhibitory neurotransmitter of the central nervous system. It is known that low levels of endogenous GABA are associated with seizure disorders (such as those involved in epilepsy, alcohol withdrawal, or barbiturate withdrawal), with disorders involving involuntary movement (such as those caused by the extrapyrimidal effects of drugs, for example tardive dyskinesia) with certain psychiatric disorders (such as schizophrenia and depression) and with muscle spasticity. Blockade of the transformation of GABA to succinic acid semialdehyde, such as by irreversible inhibition of GABA-T, can elevate GABA levels in the central nervous system (CNS) and, thus provides a means for treating the disorders of the CNS associated with low GABA levels.

Certain compounds are known to be irreversible inhibitors of GABA-T and thereby to elevate brain levels of GABA. Examples are 4-aminohex-5-enoic acid ("vinyl GABA"), 4-aminohex-5-ynoic acid ("acetylenic GABA" or "ethynyl GABA") and 4-amino-hepta-5,6-dienoic acid ("allenyl-GABA") (see U.S. Pat. Nos. 3,960,927, 3,959,356, and 4,454,156; Lippert et al., Eur. J. Biochem., 74, 441 (1977); Lippert et al., Brain Research Bulletin, 5((2), 375 (1980); Jung et al., J. Neurochem., 28, 717 (1977); Palfreyman et al., GABA-Neuro-Transmitter, Alfred Benzon Symposium 12; Larsen et Editors, Munksgaard, Copenhagen, 432–446 (1979); June al., Biochemical and Biophysical Research Comm., 67, 301 (1975); Palfreyman et al., Biochemical Pharm., 30, 817 (1981); and, Jung, et al., Biochemical Pharm., 33, 3717 (1984)).

In particular, these compounds are useful as anticonvulsants for the control of seizures involved in epilepsy. Anticonvulsant activity can be demonstrated by means of standard test procedures in laboratory animals against experimentally-induced seizures. These inhibitors of GABA (γ-ethynyl 1, γ-allenyl 2, and γ-vinyl 3, GABAs) have been designed and synthesized.

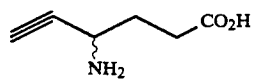

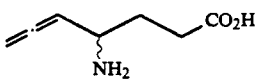

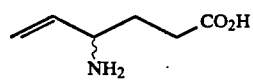

All these compounds have potential for therapeutic use and γ-vinyl GABA (vigabatrin) has already been approved in Europe as an effective drug for the treatment of epilepsy.

The biological activity of γ-allenyl GABA and γ-vinyl GABA resides in the (S)-enantiomers (P. Casara et al., Tetrahedron Letters, 25, 1891 (1984)). Conversely, (R)-γ-ethynyl GABA is more active as an anticonvulsant agent than its (S)-counterpart or racemic compound (M. J. Jung et al., Biochemistry, 17, 2628 (1978)). So far the enantiomers of γ-ethynyl GABA, γ-allenyl GABA, and γ-vinyl GABA have been produced by asymmetric synthesis (P. Casara et al., and A. Holmes et al., J. Chem. Soc., Perkin Trans. 1, 3301 (1991)) or diastereomer crystallization (M. J. Jung et al., and C. Danzin et al., Chemical and Biological Aspects of Vitamin B6 Catalysis, A. E. Evangepoulos ed., Alan R. Liss, New York, Part A, 377–385 (1984)). These methods, however, are not suitable for large-scale synthesis, since the routes are long and the yield of the final product is low.

Compounds γ-ethynyl GABA, γ-allenyl GABA, and γ-vinyl GABA are difficult targets for enzyme-based resolution techniques as well (C. J. Sih et al., Stereochem., 19, 63–125 (1898), and A. M. Klibanov, Acc. Chem. Res., 23, 114–120 (1990)). Enzymes, such as aminoacylases (H. K. Chenault et al., J. Am. Chem. Soc., 111, 6354–64 (1989)) and amino-peptidase (E. M. Meijer et al., Biocatalysts in Organic Synthesis (eds. J. Tramper et al., Amsterdam:Elsevier, 135–156 (1985)), that are normally used for the resolution of α-amino acids cannot resolve γ-amino acids. Lipases catalyze the enantioselective hydrolysis of the esters of (N-acyl)-γ-vinyl GABA, but with modest stereoselectivity. These compounds may also present a serious problem for a newly developed technique with ω-amino acid transaminases (D. I. Stirling et al., U.S. Pat. No. 4,950,606 (1990)), since γ-ethynyl GABA, γ-allenyl GABA, and γ-vinyl GABA, are designed to irreversibly inhibit the very same group of enzymes.

Here we report a simple procedure for the preparation of the enantiomers of γ-ethynyl GABA, γ-allenyl GABA, and γ-vinyl GABA by penicillin acylase-catalyzed hydrolysis of the corresponding N-phenylacetyl derivatives. Penicillin acylase (PA) from E.coli is used in industry for the preparation of 6-aminopenicillanic acid and semisynthetic β-lactam antibiotics (V. K. Svedas et al., Enzyme Microb. Technol., 2, 138 (1980)). PA is highly specific to phenylacetyl group and catalyzes its cleavage not only from penicillins, but also from amides, peptides, and esters (M. Cole, Biochem J., 115, 733 (1969); Ibid, 741; and, A. Czentirmai, Acta Microbiol. Acad. Sci. Hung., 12, 395 (1965/1966). The structure of the leaving group of the substrates hardly affects the rate constants of the hydrolytic reactions (M.

Cole, *Nature*, 203, 519 (1964), and A. L. Margolin et al., *Biochim. Biophys. Acta*, 616, 283 (1980)). The enantioselectivity of PA was exploited in the preparation of amino acids (D. Rossi et al., *Experientia*, 33, 1557 (1977) and Ibid, 41, 35 (1985)), aminoalkylphosphonic acids (V. A. Solodenko et al., *Tetrahedron*, 47, 3989 (1991)), esters and alcohols (C. Fuganti et al., *Tetrahedron Letters*, 44, 2575 (1988), and H. Waldman, 30, 3057 (1989)), although the hydrolysis of an ester bond normally results in products with modest optical purity. Recently, the high enantioselectivity of PA in the acylation reaction was demonstrated in the synthesis of a new carbacephalosporin, locarbef (M. Zmijewski et al., *Tetrahedron Letters*, 32, 1621 (1991)).

SUMMARY OF THE INVENTION

We reasoned that the broad substrate specificity of PA towards leaving groups combined with its high enantioselectivity will be useful in the synthesis of optically pure GABA-T inhibitors γ-ethynyl GABA, γ-allenyl GABA, and γ-vinyl GABA. This indeed, turned out to be the case. The resolution procedure is outlined in Scheme I.

SCHEME I
PA-Catalyzed Resolution of GABA-T Inhibitors

A.
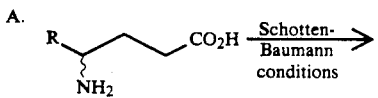

FORMULA 1

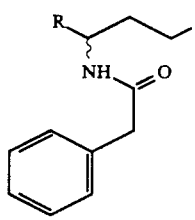

FORMULA 2

B.
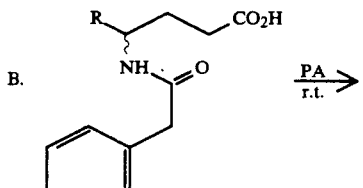

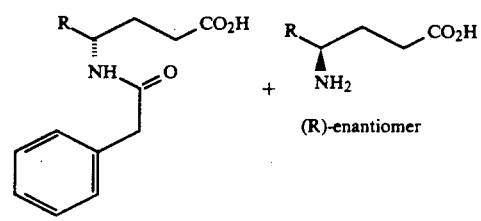

(R)-enantiomer

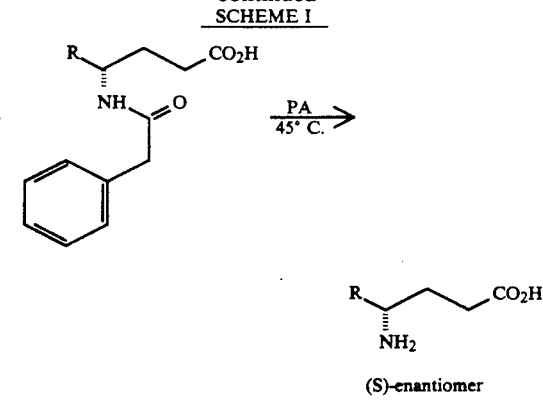

(S)-enantiomer

In short, the process is for the enzymatic resolution of a racemic mixture of stereospecific GABA-T inhibitors of the structure according to Formula 1. The process involves preparing (A.) a N-phenylacetyl derivative of a compound according to Formula 1, wherein R is $H_2C=CH-$, $HC\equiv C-$, or $H_2C=CH-HC=CH-$, to produce a racemic mixture consisting of the (S)-(N-phenylacetyl) enantiomer and the (R)-(N-phenylacetyl) enantiomer of a compound according to Formula 2, wherein R is defined as above. This procedure is carried out under Schotten-Baumann conditions and is well-known to those skilled in the art. Next, (B.) the racemic mixture of the compound according to Formula 2 is contacted with penicillin acylase to prepare the (S)-(N-phenylacetyl) enantiomer of the compound according to Formula 2 and to produce the (R)-enantiomer of the compound according to Formula 1. Then (C.) the (S)-(N-phenylacetyl) enantiomer of the compound according to Formula 2 is hydrolyzed to form the (S)-enantiomer of the compound according to Formula 1. Preferably, this hydrolysis is carried out with the enzyme penicillin acylase. The (R)- and the (S)-enantiomers of the compounds according to Formula 1 are then separated by methods well-known in the art.

DETAILED DESCRIPTION OF THE INVENTION

Example 1

In a typical experiment, 0.7 g of penicillin acylase immobilized on Eupergit C, was suspended in a solution of (N-phenylacetyl)-vinyl GABA (1.0 g; 4 mmol) in 35 ml 0.1 M phosphate buffer, pH 7.8. The mixture was stirred at room temperature (r.t.) for 5 hours. Then the solution was adjusted to pH 2 and the remaining substrate was extracted with $CH_2Cl_2$ to give (S)-(N-phenylacetyl)-vinyl GABA (organic layer) and (R)-γ-vinyl GABA (aqueous). Since the chemical deacylation of (S)-(N-phenylacetyl)-vinyl GABA under acid conditions results in the formation of byproducts the same enzyme was used for the deacylation of (S)-(N-phenylacetyl)-vinyl GABA. To achieve an effective hydrolysis, a larger amount of Eupergit-PA (1.5 g), higher reaction temperature (45° C.), and longer reaction time (2 days) were used. When the reaction was complete (HPLC) the Eupergit-PA was filtered off and phenylacetic acid was extracted with $CH_2Cl_2$ from acidic solution (pH 2). The aqueous solution of both (R)- and (S)-γ-vinyl GABA were subjected to ion-exchange chromatography (Dowex 1×2−100 (OH−)) followed by lyophilization. The enamtiomers of γ-ethynyl GABA and γ-allenyl GABA were prepared by the same procedure (Table 1).

TABLE 1

| $R^a$ | Reaction rate[b] (%) | (R)-γ-amino acid yield (%)[c]; ee (%)[d] | (S)[e]-γ-amino acid yield (%); ee (%) | E[f] |
|---|---|---|---|---|
| Ethynyl | 100 | 48; >96 | 41; >83 | >100 |
| Allenyl | 46 | 54; >75 | 43; >98 | 20 |
| Vinyl | 39 | 47; 78 | 35; 99 | 17 |

[a]N-Phenylacetyl derivatives of γ-ethynyl GABA, γ-allenyl GABA, and γ-vinyl GABA were prepared under Schotten-Baumann conditions.
[b][S] = 50 mm; pH 7.8:25° C.
[c]Isolated yields for lyophilized compounds.
[d]Enantiomeric excess for lyophilized compounds was determined by gas chromatography using Chirasil-Val column (Chrompack) according to the procedure of J. Wagner, et al., Chromatography, 392, 211 (1987).
[e]The absolute configurations were assigned by direct comparison of $[α]_D$ with authentic samples.
[f]The E values were calculated from the yields and the ee's of the (R)-enantiomers (C. S. Chen, et al., J. Am. Chem. Soc., 104, 7294 (1982)).

One can see that the pharmaceutically important (S)-enantiomers of γ-allenyl GABA and γ-vinyl GABA, as well as both enantiomers of γ-ethynyl GABA have been synthesized in good yield and high optical purity. It should be stressed that this procedure employs inexpensive commercially available immobilized enzyme, which has already proven its excellent qualities on a very large scale.

What is claimed is:

1. A process for the enzymatic resolution of a racemic mixture of a compound of the structure according to Formula 1
wherein R is $H_2C=CH-$, $HC\equiv C-$, or $H_2C=CH-HC=CH-$, comprising:
   (a) in solution preparing a N-phenylacetyl derivative of the compound according to Formula 1, wherein R is defined as above, to produce a racemic mixture consisting of the (S)-(N-phenylacetyl) enantiomer and the (R)-(N-phenylacetyl) enantiomer of

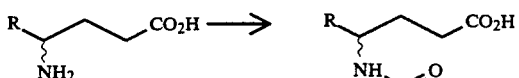

FORMULA 1

FORMULA 2 a compound according to Formula 2, wherein R is defined as above;
   (b) contacting the racemic mixture of the compound of Formula 2 with penicillin acylase at approximately room temperature to produce the (R)-enantiomer of the compound according to Formula 1;
   (c) extracting the (S)-(N-phenylacetyl) enantiomer of a compound according to Formula 2 with an organic solvent thereby creating a solution having an organic layer and an aqueous layer;
   (d) removing the aqueous layer of the solution containing the (R)-enantiomer of the compound according to Formula 1;
   (e) hydrolyzing the (S)-(N-phenylacetyl) enantiomer of the compound according to Formula 2 to form the (S)-enantiomer of the compound according to Formula 1.

2. The process according to claim 1 wherein R is $H_2C=CH-$.

3. The process according to claim 1 wherein R is $HC\equiv C-$.

4. The process according to claim 1 wherein R is $H_2C=CH-HC=CH-$.

* * * * *